US008428738B2

(12) United States Patent
Valencia

(10) Patent No.: US 8,428,738 B2
(45) Date of Patent: Apr. 23, 2013

(54) COUPLED NEURAXIAL MESOSCOPIC DESYNCHRONIZATION ELECTROSTIMULATION THERAPY (CNMDET) METHOD

(76) Inventor: Andrew D. Valencia, Taos, NM (US)

( * ) Notice: Subject to any disclaimer, the term of this patent is extended or adjusted under 35 U.S.C. 154(b) by 539 days.

(21) Appl. No.: 12/583,899

(22) Filed: Aug. 26, 2009

(65) Prior Publication Data

US 2011/0054564 A1    Mar. 3, 2011

(51) Int. Cl.
*A61N 1/18* (2006.01)
(52) U.S. Cl.
USPC .................................. 607/50; 607/45; 607/46
(58) Field of Classification Search .................... 607/46, 607/148, 2, 45, 117, 48, 50
See application file for complete search history.

(56) References Cited

U.S. PATENT DOCUMENTS 7,117,034 B2   10/2006  Kronberg
7,489,964 B2    2/2009  Suffin et al.

*Primary Examiner* — Carl H Layno
*Assistant Examiner* — Paula J Stice

(57) ABSTRACT

This novel therapeutic (reparative, etiotropic not merely symptomatolytic) electrostimulatory method hereinafter referred to as Coupled Neuraxial Mesoscopic Desynchronization Electrostimulation Therapy (cNMDET) is comprised of a varied combination of progressively sequenced electrode placements and its clinically targeted areas which are comprised of the CNS [regions of the brain and spinal cord including, but not limited to, the underlying clinicopathologic mechanisms of the ANS] and clinically involved components of the PNS variably coupled in such a manner as to apply this therapeutic electrostimulation (reparative modulation) along the coursing path (longitudinally) of the targeted neural pathway over a segment and/or in its entirety, as well as, the utilization of patterned applications for involved joints, muscles, fascia, ligaments, tendons and areas involved in inflammatory processes of clinical significance accomplished through the application of, preferably, but not limited to, Coupled Neuraxial Transcutaneous Electrical Nerve Stimulation (cNTENS) and Coupled Neuraxial Transcranial Direct Stimulation (ctDCS$_n$).

8 Claims, 4 Drawing Sheets

FIG. 1- NMDET PLACEMENT ILLUSTRATION OV1
Sample Demonstration of 'Neural Tube Technique' (NTT)

FIG. 1A

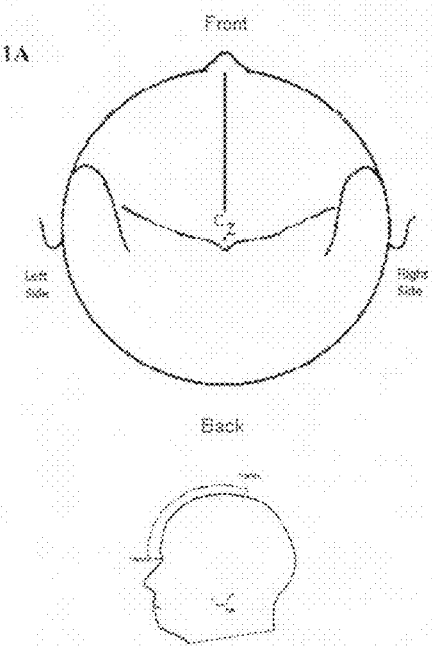

FIG. 1C

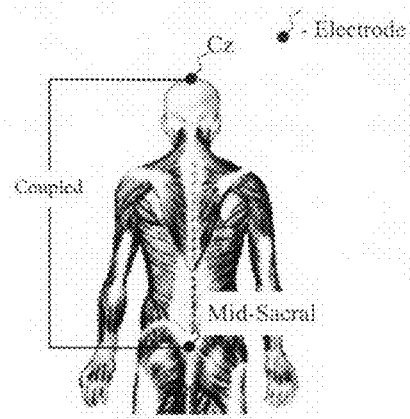

Example of Targeted Area for 'Neural Tube' Technique Coupled Electrode (the 'sacral outflow area')

FIG. 1B

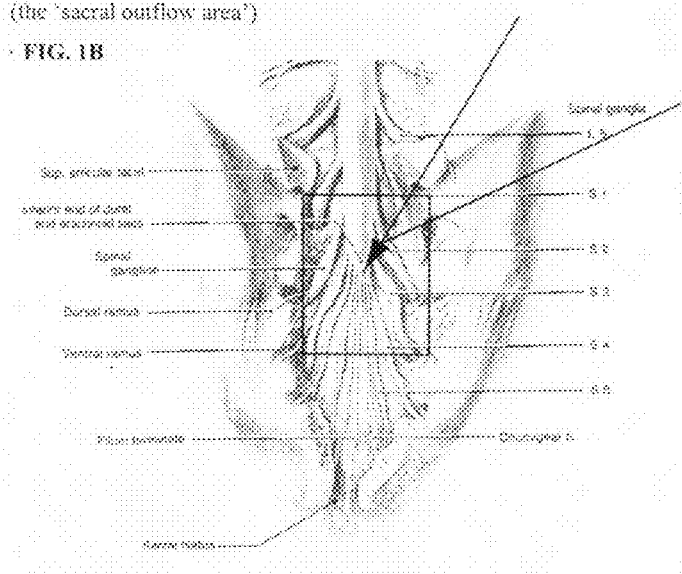

This particular example of a targeted area for the 'Neural Tube' technique coupled electrode. This illustration exemplifies one of the many currently anticipated potentially suggested placements as provided for by the patient-specific, controlling treatment protocol.

FIG. 2- NMDET PLACEMENT ILLUSTRATION OV2
Diagram of One Example of NMDET with Targeted Peripheral Nerve Application

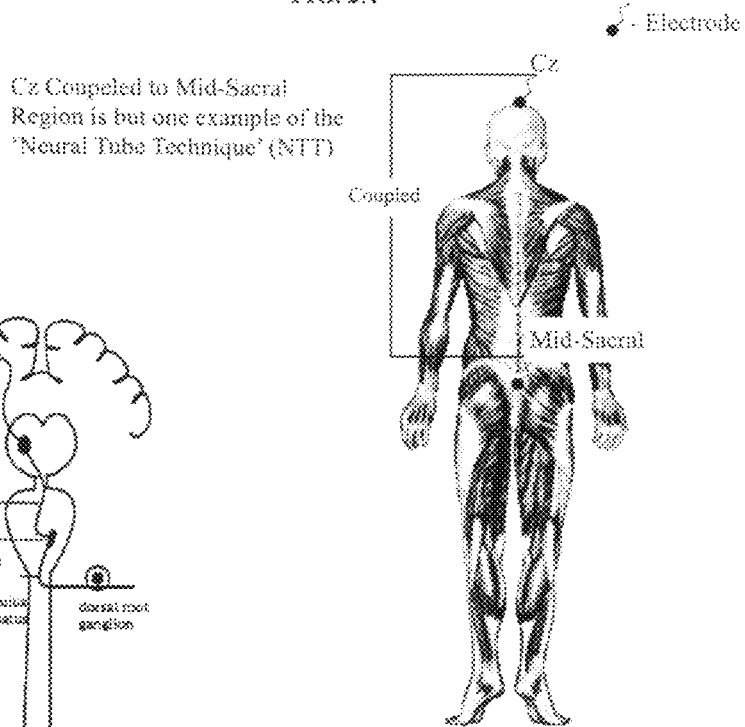

FIG. 2A

Cz Coupled to Mid-Sacral Region is but one example of the 'Neural Tube Technique' (NTT)

FIG. 2C

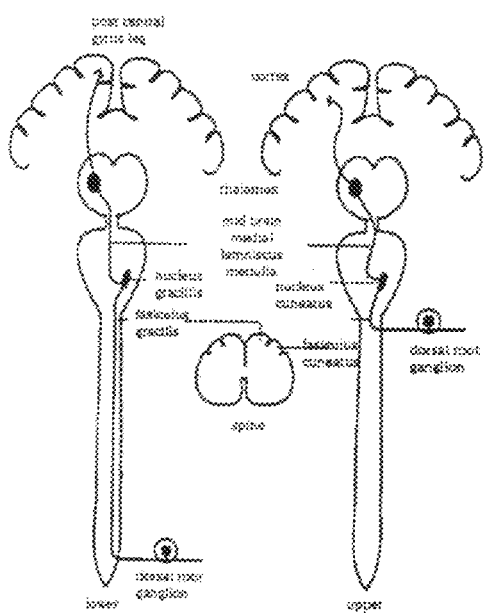

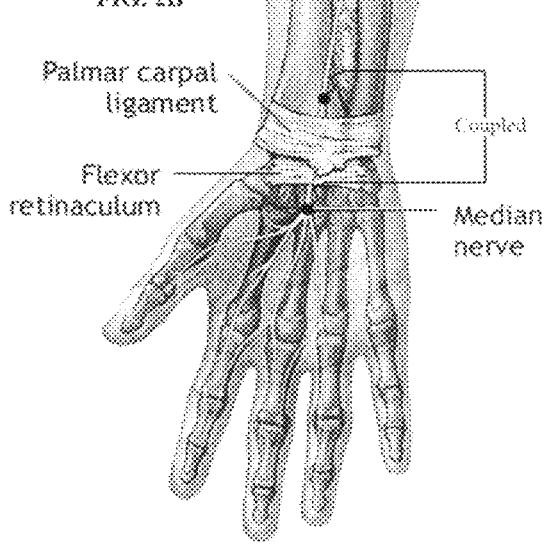

FIG. 2B

The phrase 'longitudinally coursing path' when indicated by the 'patient-specific, controlling treatment protocol' is meant to indicate an entire targeted nerve or nerve segment, as is commonly understood in the traditional medical industry. FIG. 2C provides for an overview of general neuropathways which may be central and/or peripheral. Serving as only two examples of such placements, are identified in the placement of a coupled electrode on the distal portion of the 'median nerve' in FIG. 2B or the 'sacral outflow area' in FIG. 1B when that placement is coupled by protocol to a second stimulating electrode located at Cz shown in FIG. 1A.

FIG. 3- NMDET PLACEMENT ILLUSTRATION OV3
Diagram of One Example of NMDET with Targeted Muscle Application

FIG. 3A

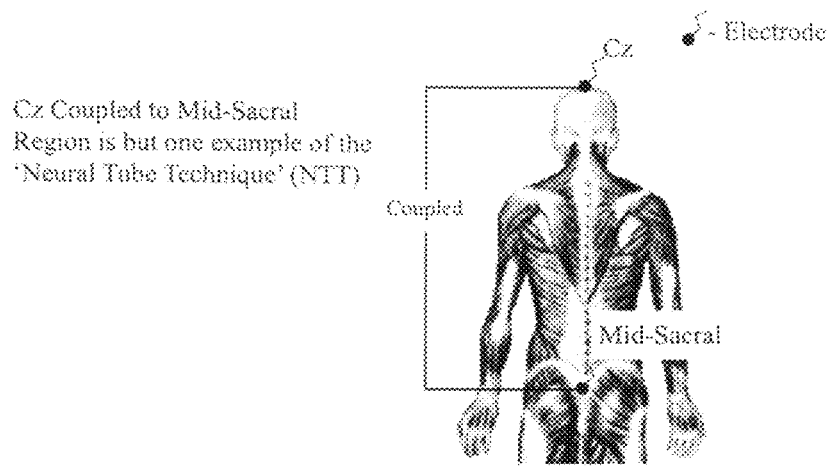

Cz Coupled to Mid-Sacral Region is but one example of the 'Neural Tube Technique' (NTT)

FIG. 3B

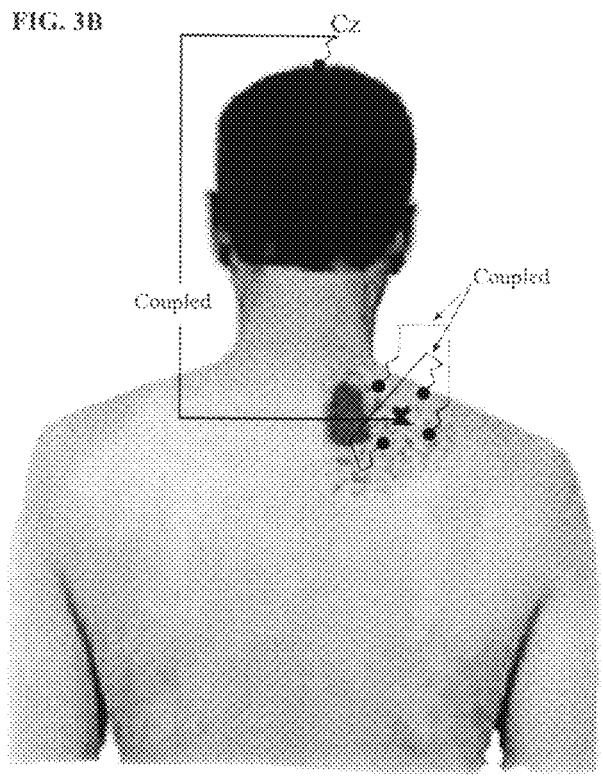

'X'- Trigger Point (TrP), however when coupled with 'Cz', denotes placement of 2nd electrode
Grey- Solid (more intense) & Stippled (less intense) represents referred pain areas of the TrP

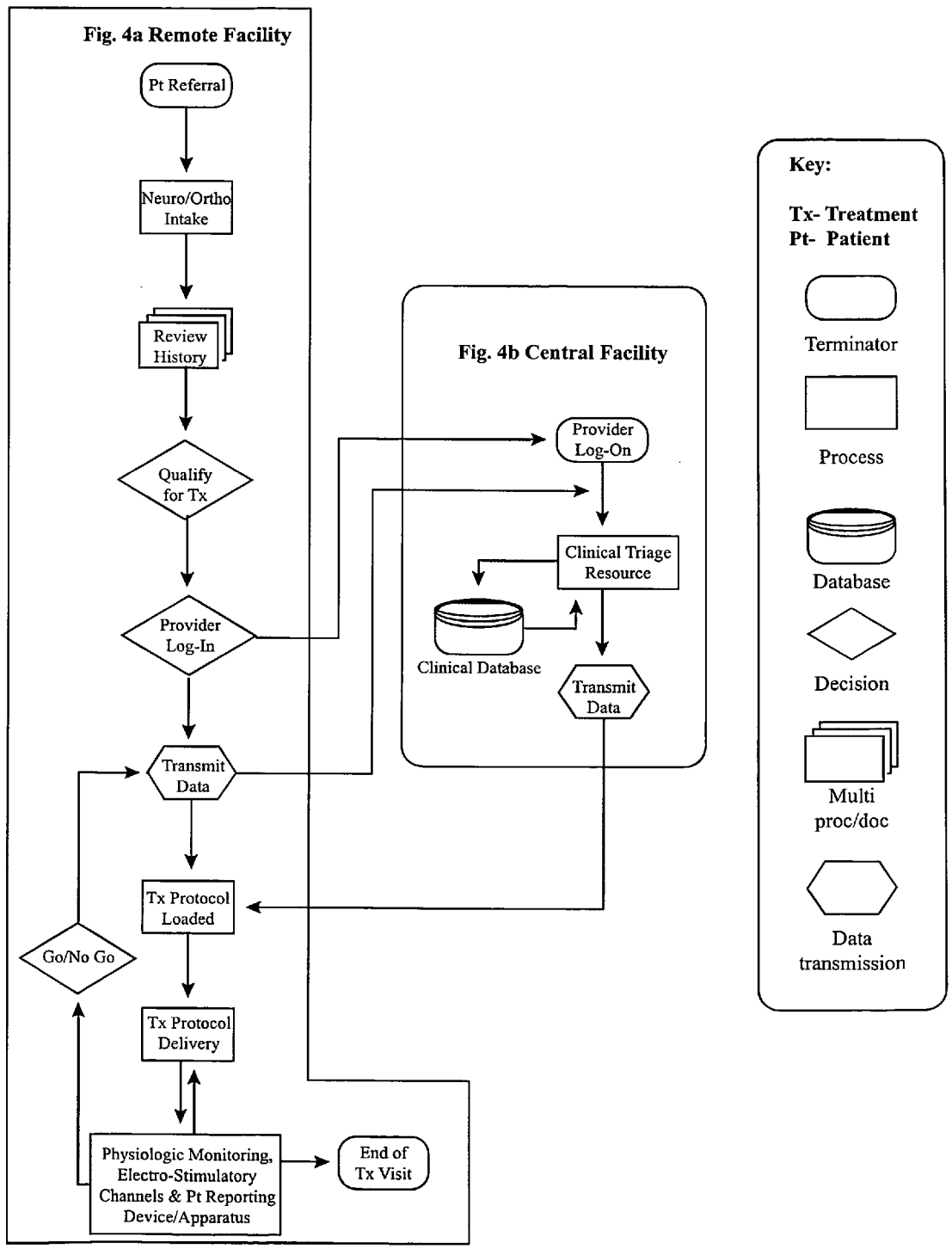
Fig. 4 Process Flow Chart

COUPLED NEURAXIAL MESOSCOPIC DESYNCHRONIZATION ELECTROSTIMULATION THERAPY (CNMDET) METHOD

BACKGROUND OF THE DISCLOSURE

1. Technical Field of the Invention

This novel therapeutic (reparative, etiotropic not merely symptomatolytic) electrostimulatory method hereinafter referred to as Coupled Neuraxial Mesoscopic Desynchronization Electrostimulation Therapy (cNMDET) is comprised of a varied combination of progressively sequenced electrode placements based on the clinically determined targeted areas which are further comprised of the central nervous system (CNS) [regions of the brain, spinal cord and intervening structures including, but not limited to, the underlying (contributory) clinicopathologic mechanisms of the autonomic nervous system (ANS)] and clinically involved components of the peripheral nervous system (PNS) variably coupled as provided for by the patient-specific, controlling treatment protocol in such a manner as to apply this therapeutic electrostimulation method along the coursing path (longitudinally) of the targeted neural pathway over a segment and/or in its entirety (the full expanse possible of the CNS and PNS), as well as, the utilization of patterned applications for involved joints, muscles, fascia, ligaments, tendons and areas involved in inflammatory processes of clinical significance accomplished through the application of, preferably, but not limited to, Coupled Neuraxial Transcutaneous Electrical Nerve Stimulation (cNTENS) and Coupled Neuraxial Transcranial Direct Stimulation (ctDCS$_n$). The phrase 'coupled neuraxial' herein will be used to denote the method of providing therapeutic electrostimulation, longitudinally, to the CNS (regions of the brain, spinal cord and intervening structures) including, but not limited to, the ANS and clinically involved components of the PNS and other tissues, i.e., joints, muscles, fascia, ligaments, tendons and areas involved in inflammatory processes of clinical significance, variably coupled as provided for by the patient-specific, controlling treatment protocol in such a manner as to apply the therapeutic electrostimulation along the coursing path (longitudinally) of the targeted neural pathway over a segment and/or in its entirety. Of critical importance is the incorporation of this cNMDET method approach applied to all clinically targeted areas in a highly individualized manner, which is patient by patient. Strict compliance to the controlling treatment protocol is critical to protecting a favorable outcome and guarding the 'patient experience'. The progressive sequencing of electrode placements in each controlling treatment protocol is based on the arduous clinical identification of all the clinically involved areas and, to the extent they are clinically contributive to the patient's underlying etiologic mechanisms as well as those contributing to their perception of pain, if different, in such a manner as to achieve 'true remediation' not 'merely adaptive recovery' or simply the masking of the perception of pain. The capacity to target the reversal of maladaptive neuroplastic/metaplastic changes that subserve, in part or in whole, pain, as well as, other contributing processes (clinicopathologic mechanisms), including, but not limited to, inflammatory responses and secondary ANS changes is one of the core achievements of this method's therapeutic value. Serving as a therapeutic portal to this method are the processes of 'priming' and 'preconditioning' which allow the body's inherent ever vigilant feedback loops capable otherwise of blocking many other therapeutic approaches to now allow the experience of reparative modulation achieved by the cNMDET method which has been individually formulated as a critical quality of each treatment protocol. Without these method patent related processes of priming and preconditioning, as well as, the subsequently progressive sequencing, individualized patterned therapeutic electrostimulatory (modulatory) formulations, the human body is innately capable of negating the intended modulation of same, by overriding the intended applied reparative neuromodulation via several processes such as 'adaptation'.

Of equal importance to this novel method as is priming and preconditioning is the utilization of another novel component of cNMDET, the 'Neural-Tube Technique' (NTT). NTT is the electrostimulatory coupling of the brain, intervening neural structures and spinal cord, to include, but not be limited to, the 'sacral outflow' area (the cauda equina area). The anatomical expanse, i.e., distance between coupled electrodes, may be quite narrow ranging to the full incorporation of the brain's most superior/rostral extreme, coupled to the spinal cord's most inferior/caudal position of the CNS to include the anatomical area of the cauda equina ('sacral outflow area'). This expanse would include all the potential coupled placements contained therein. It is anticipated that one or more coupled electrodes (including arrays of electrodes) throughout this expanse are to be used as provided for by the controlling treatment protocol.

In its preferred embodiment, the cNMDET method would be applied utilizing an apparatus/device such as the multifunctional Algotron, a combination Coupled Neuraxial Transcutaneous Electrical Nerve Stimulation (cNTENS) and Coupled Neuraxial Transcranial Direct Stimulation (ctDCS$_n$) apparatus/device. This apparatus/device incorporates the mandatory utilization of multiple physiologic monitoring channels and multiple therapeutic electrostimulatory channels. This novel cNTENS/ctDCS$_n$ apparatus/device is the subject of a post-election divisional patent application.

Resulting from several decades of clinical experience, the resultant understanding is that any method application to approach delivering therapeutic (reparative) electrostimulatory modalities such as the subject matter of this method application referred to as Coupled Neuraxial Mesoscopic Desynchronization Electrostimulation Therapy (cNMDET) must address, as a practical matter, the properties of applicable neural pathway synaptic associative activity and volume related cooperativity both in sufficient levels/degrees of achievement if it claims to provide true remediation, i.e., etiotropic, as opposed to only achieving a temporizing or masking effect of the presenting symptoms, i.e., symptomatolytic. It is my belief that to the extent time is spent on symptomatic approaches at the expense of accomplishing true remediation is with that passage of time comes the increasing probability of maladaptive recovery. Further, to achieve therapeutic (reparative) modulation in the targeted CNS and/or PNS the therapeutic regimen must contemporaneously address and, in fact, incorporate the body's entire adaptive mechanistic capacity (both that of the CNS and PNS individually but of greater importance, their collective interdependent states) and the potentially significant influences of clinicopathologic neuroplastic and metaplastic changes that clinically evolve until the underlying clinicodynamics are repaired.

2. Scope of the Invention in Terms of Therapeutic Needs Fulfillment

The established utility of this patent method can best be illustrated by providing a sample range of the pain related diagnostic entities targeted to date by this method. This list is only a partial list of those diagnostic entities as it relates to pain, provided here only to help illustrate the extensive scope of application of this method patent: Chronic Pain, Neuropathic Pain, Fibromyalgia Pain Syndrome, Dysautonomia, Multiple Sclerosis (MS), Barré-Liéou Syndrome, Radiculitis/Radicular Pain Syndrome, Brachial Plexitis (Parsonage Turner Syndrome) (neurogenic, non-compressive), Myofascial Pain Syndrome, Myofascial Trigger Points, Carpal Tunnel Syndrome, Tarsal Tunnel Syndrome, Phantom Limb Pain Syndrome, Parietal Pseudothalamic Pain Syndrome, Pseudothalamic Pain Syndrome, Adhesive Capsulitis, Rotor Cuff Syndrome, Bursitis, Migraines (neurogenic), Paratrigeminal Syndrome, Trigeminal Neuralgia, Temporomandibular joint disorder (TMJD) or TMJ syndrome, Tennis Elbow (Lateral Epicondylitis), Pain secondary to Klippel-Feil Syndrome and Plantar Fasciitis.

Goethe was attributed with saying: "A man sees only what he knows". I know our clinical outcomes: I see a future for this application as we know it or as it may be ultimately manifested through the understandings/contributions of others. At the heart of this application submission is the topic of 'pain', 'persistent clinical pain', pain that causes patients to seek treatment. Despite the scientific purview of this submission, one must never loose site of the ultimate obligation/responsibility we have to continually endeavor to improve on the 'patient experience' in direct appreciable terms as manifested in their quality of life experiences. The genesis of this method application were the gnawing questions: What causes the development of 'persistent clinical pain' appearing after only a few days post precipitating event for some patients, 7-10 days in other patients, while yet other patients report the temporal onset of the 'persistent clinical pain' weeks or months after a known precipitating event, if any is identifiable; and, why have the treatments for same produced such poor statistical outcomes? I am not satisfied with the almost dismissive tone that comes with: "it's individualized" with no further direct interpretation (import) to the presenting patient. Yes, I believe each patient comes with their individual set of unique genetic codes and totality of experiences, but, I believe there does exist a commonality of CNS and PNS clinical neuroplastic clinicodynamic changes that commonly occur or are recruited in the case of 'persistent clinical pain'. It is that commonality of induced mechanistic changes in the CNS and/or PNS that this method application, along with the post-election components, were brought into existence to address. It is my most solemn prayer that this patent application will lead to the appropriate attention and assistance necessary in further developing this concept to the fullest extent of its merited potential.

This method application referred to as Coupled Neuraxial Mesoscopic Desynchronization Electrostimulation Therapy (cNMDET) addresses the critical properties of applicable neural pathway synaptic associative activity and volume related cooperativity, that must be additionally recruited, both, in sufficient levels/degrees of achievement in support of true reparative modulation of the CNS and/or PNS. The complex formulation of the priming, preconditioning and treatment phases as provided for by the controlling treatment protocol promotes this, heretofore rather illusive, therapeutic (reparative) modulation in the targeted CNS and/or PNS by, in fact, synergistically incorporating the body's entire adaptive mechanistic capacity in their individual and collective states. Additionally, cNMDET enhances the supportive underlying neurometabolic capacities of neural structure and function that are therapeutically induced resulting from the application of cNMDET and is of critical importance to sustaining the desired and therapeutically sought level of reparative processes which have been, heretofore, woefully lacking in all other therapeutic approaches.

3. Description of the Related Prior Art

It is generally well known that the application of some forms of electrical stimulation to the body of a patient in the area of soreness or pain can have a therapeutic and anesthetizing effect, although the physiological basis is not completely understood. As addressed in U.S. Pat. No. 3,835,833, the application of electrostimulation via electrodes placed on the body (without mention of intervening targeted longitudinal neural pathway electrode placements) of a patient heretofore utilizing acupuncture points or generally in the area of reported pain (independent of underlying neural structure) causing various therapeutic effects such as local anesthesia or relaxation of muscle. The present invention advances in clinical import in orders of magnitude in specificity of application and scope of effectiveness based on the novel method referred to as cNMDET.

As it pertains to the various commercially available Transcutaneous Electrical Nerve Stimulation (TENS) devices, including but not limited to, Cranial Electrical Stimulation (CES) devices, manufacturers and practitioners utilizing such devices appear to be woefully deficient and possibly clinically negligent in their apparatus/device design with their recommended treatment protocols. One of the areas of greatest concern is the absence of recommendations and/or incorporation of critically essential concomitant (contemporaneous) patient physiologic monitoring. Designed to correct for the above referenced deficiencies, our multifunctional Algotron, a combination Coupled Neuraxial Transcutaneous Electrical Stimulator (cNTENS)/Coupled Neuraxial Transcranial Direct Current Stimulation (ctDCS$_n$) apparatus/device, is the subject of a post-election divisional patent to be subsequently filed. Our multifunctional Algotron apparatus/device is, in part, comprised of a novel electrostimulatory therapeutic capacity and incorporates a comprehensive range of 'in-process' (real-time) contemporaneous physiologic diagnostics and monitoring channels allowing for the most effective application of cNMDET. Further, the Algotron is designed to produce true remediation, targeting etiotropic changes, not merely perpetuating one more of the many producing iatrogenic dependences on modalities that can only be viewed as being simply temporizing, masking or symptomatolytic.

The first modern, patient-wearable TENS was patented in the United States in 1974. [U.S. Pat. No. 3,817,254] It was initially used for testing the tolerance of chronic pain patients to electrical stimulation before implantation of electrodes in the spinal cord dorsal column. [Surg Neurol 2 (1): 39-40] The electrodes were attached to an implanted receiver, which received its power from an antenna worn on the surface of the skin. Of major concern for this device is the morbidity/mortality associated with required surgical implantation. This concern is addressed with the cNMDET method in that there is no known morbidity or mortality associated with its intended usage. Additionally, another deficiency is that as conceived there is no concomitant (contemporaneous) patient physiologic monitoring capacity once the patient becomes ambulatory in the post-insertion phase. Lastly, there is no provision for the treatment of the entire potentially involved neural pathway especially when the patient's condition, as is frequently seen, involves central sensitization, secondary inflammatory processes, etc. imposing secondary clinicopathologic neuroplastic and metaplastic processes which is of critical importance in guarding the clinical evolution and eventual outcome of each case.

Heretofore, generally, electrostimulatory approaches for the treatment of pain are thought to work in some combination of two basic mechanisms. First, on a high frequency, by selectively stimulating certain 'non-pain' nerve fibers to send signals to the brain that is thought to 'block' [essentially masking the pain signals by altering the perception of pain without any therapeutic (etiotropic) import] other nerve signals carrying pain messages. The claim of this approach is relatively common despite hard science indicating reported negative side-effects such as those of excitotoxicity, encouragement of a range of secondary maladaptive neuroplastic/metaplastic changes (including, but not limited to, 'kindling' and 'dynamic entrainment'). Second, on low frequencies, TENS is thought to transiently stimulate the production of endorphins, the body's natural pain-relieving hormones. Historically and generally, the device was usually used for 30 minutes, several times a day on average, and was controlled by the user rather than a licensed health professional which for obvious clinical reasons is thought by many in a position to evaluate same to be contraindicated because of the lack of continuous supervision. In light of the aforementioned deficiencies, the typical range of claims made for these devices and related methodology is so conspicuously vast as to require additional due diligence by all potentially or currently subscribing practitioners and the targeted patient population at large before applying same. One supporting example of escalating concerns pertaining to the methodology, as well as, the device's design of Cranial Electrotherapy Stimulation (CES) is the published finding of the Federal Drug Administration (FDA). Noteworthy is the specific reference therein of applicability to the exclusion of Transcranial Direct Current Stimulation (tDCS) and Transcranial Magnetic Stimulation (TMS) for which the cNMDET method was ideally designed. Compelling are the statements found in the below excerpt from the FDA Executive Summary prepared for the meeting of the Neurologic Devices Panel pertaining to CES, but to be clear, not 'tDCS' which includes our multifunctional Algotron, a combination cNTENS and ctDCS$_n$ novel apparatus/device.

"Among studies that reported a clinical benefit of CES, few can be considered rigorous, high quality clinical studies.

FDA believes that there are basic elements that should be present in any study seeking to evaluate the effectiveness of CES, including, but not limited to: randomized with a sham control group, eligibility criteria based on a specific diagnosis, a clinically relevant measure of effectiveness, adequately powered sample size, predefined success criteria, and consideration for durability of effect. None of the studies identified in the literature review met all of these criteria. Regardless of the main findings, many of these studies had key limitations in study design that likely obscure the true effectiveness of CES. For example, only 12.8% (5 of 39) of the studies reported using the DSM criteria to diagnose depression, anxiety or insomnia. Without the use of established and clinically accepted diagnostic criteria, it is unclear what psychiatric condition, if any, CES was attempting to treat in the remaining 87.2% of studies. Furthermore, the body of research lacks cohesion in the device model, dosage and duration studied. While the literature review was not limited to cleared devices, FDA sought to ensure that the output characteristics were generally consistent with the ranges of values we have evaluated in premarket submissions. In the papers that we reviewed, there were 25 different models of CES devices used, excluding 7 that were custom built and some studies did not report Page 36 of 83 the CES device model. Since the electrical output characteristics also vary across the different device types (see Table 16), making assumptions about the applicability of positive findings by one CES device to other CES devices is not possible.

Other important study limitations that have been previously mentioned include: small sample size, placebo effect (due to either no masking or unsuccessful masking) and inadequate statistical methods. In the absence of a reasonable assurance of effectiveness, a key concern stemming from our review of the literature is that use of CES in lieu of more effective, proven therapies may present undue risk to patients whose psychiatric conditions may worsen if untreated."

The benefit of the traditional methodology utilized by electrostimulatory devices such as a TENS device as it pertains to the treatment of pain remains, heretofore, somewhat controversial in the traditional medical community. One review from 2007 felt that the evidence supports a benefit in chronic musculoskeletal pain [Pain 130 (1): 157-165. DOI:10.1016/j.pain.2007.02.007] while another review from the Cochrane Collaboration in 2008 deemed the evidence of poor quality and thus no conclusions where possible regarding chronic pain. [Cochrane database of systematic reviews (Online) (3): CD003222] Results from a task force on neck pain, in 2008, found no clinically significant benefit to TENS for the treatment of neck pain when compared to placebo treatment. [Spine 33 (4S Supplement): S5-7. DOI:10.1097/BRS.0b013e3181643f40] A 2010 review did not find evidence to support the use of TENS for chronic low back pain. [Neurology 74 (2): 173-6 and Cochrane database of systematic reviews (Online) (4): CD003008] There is tentative evidence that it may be useful for painful diabetic neuropathy. [Neurology 74 (2): 173-6] It is for these and other reasons that the cNMDET method and Algotron apparatus/device was invented.

It is, at a minimum, noteworthy and considered by this author/inventor to be imperative for all practitioners and potentially targeted patients to be aware of the full realm of the published contraindications and warnings referenced below associated with the use of some electrostimulatory devices such as the TENS unit in the literature as of today:

This device should be used only under the 'continuous supervision of a physician'.

Extreme caution should be exercised in patients with known myocardial disease, arrhythmias or epilepsy.

Electronic equipment such as EKG monitors and EKG alarms may not operate properly when a TENS is in use.

Also, this device should not be used over metal implants or sleep apnea monitors.

TENS, as utilized heretofore, is ineffective for pain of 'central' origin, for example, headaches, hepatitis, cystitis, etc.

TENS, as utilized heretofore, is of no curative value.

TENS, as utilized heretofore, is a symptomatic treatment that suppresses pain sensation that would otherwise serve as a protective mechanism on the outcome of the clinical process.

Safety of TENS devices for use during pregnancy or delivery has not been established.

TENS devices, as utilized heretofore, can affect the operation of demand type cardiac pacemakers.

Do not use TENS on the eyes.

Do not place electrodes directly over the carotid sinus nerves or arteries and laryngeal or pharyngeal muscles.

Do not apply TENS for undiagnosed pain syndromes until etiology (actual cause) is established.

Do not place a TENS electrodes as utilized heretofore in any position that allows current to flow transcerebrally (through the head).

Do not use TENS on broken skin or on areas where normal sensation is absent.

Do not use TENS on children under the age of 12 unless under medical supervision.

Additionally, there is a growing consensus that the published (prescribed) utilization of electrostimulatory devices such as TENS devices heretofore may be promoting adverse neuromodulatory effects that simply promote the 'masking' of pain while concomitantly possibly promoting exacerbating maladaptive neuroplastic changes likely at the expense of true remediation. In fact, the mechanisms employed to perfect the 'masking' of pain perception are known to often be responsible for a degree of deleterious 'maladaptive' neuroplasticity and metaplastic changes that may ultimately contribute to the 'chronification' of pain. [Flor, et al '94]

SUMMARY OF THE INVENTION

In the preferred embodiment of this method patent application, the prescribed use of this novel method patent, referred to as the cNMDET method, was developed for the formulated delivery of therapeutic electrostimulation to or in some combination of the central nervous system (CNS) [regions of the brain, spinal cord and intervening structures including but not limited to the underlying (contributory) clinicopathologic mechanisms of the autonomic nervous system (ANS)] and clinically involved components of the peripheral nervous system (PNS) variably coupled as provided for by the controlling treatment protocol in such a manner as to apply this therapeutic electrostimulation along the coursing path (longitudinally) of the targeted neural pathway over a segment and/or in its entirety, as well as, the utilization of patterned applications for involved joints, muscles, fascia, ligaments, tendons and areas involved in inflammatory processes of clinical significance accomplished through the application of, preferably, but not limited to, Coupled Neuraxial Transcutaneous Electrical Nerve Stimulation (cNTENS) and Coupled Neuraxial Transcranial Direct Stimulation (ctDCS$_n$). This therapeutic method patent application for the treatment of pain has produced an effective treatment for a broad range of pain patients over many diagnostic entities. In its preferred embodiment the delivery of this method would be accomplished utilizing a novel treatment apparatus/device, a combination Coupled Neuraxial Transcutaneous Electrical Stimulator (cNTENS)/Coupled Neuraxial Transcranial Direct Current Stimulation (ctDCS$_n$) collectively referred to as a multifunctional Algotron utilized by a remote licensed Provider communicating over a continuous web-based, bidirectional connection network to a central facility for the facilitation of continuous monitoring of the patient's contemporaneous response to treatment in support of the local provider's monitoring and provides assistance to that local licensed provider by way of the documentation and continuous review of the evolution of the therapeutically coordinated process from the longitudinal perspective. The multifunctional Algotron's unique user interface allows for the central facility to download requests for additional data (patient identifying, supplemental clinical, etc.) as would be considered to be circumspectly necessary to the development of what would be considered by the central facility to be the best controlling treatment protocol possible for that patient under treatment on that visit at that time. This central facility generated protocol is then downloaded to the originating local licensed provider for execution of same. The development of the patient-specific, controlling treatment protocol, in this preferred embodiment, is critically facilitated by the use of a clinical-outcomes knowledge-based algorithmic database/ software program, one such program herein referred to as the AlgoNeuroMatrix (ANM), for the ongoing management of various pain treatment components across a network of professional providers, and various clinical resources, collectively referred to as the Clinical Triage Resource for the purpose of improving clinical outcomes for patients being treated for pain. The Algotron and AlgoNeuroMatrix are the subjects of post-election divisional patents to be subsequently filed.

In its preferred embodiment, this method patent, cNMDET, is comprised of, but not limited to, the targeting of activity in the 'mesoscopic', as well as, 'macroscopic' scales. The mesoscopic scale refers to the subdiscipline of condensed-matter that focuses on the properties of solids in a size range intermediate between bulk matter and individual atoms or molecules. Stated differently, the mesoscopic scale refers to the scale at which one can reasonably discuss the properties of a material or phenomenon without having to discuss the behavior of individual atoms. The causal relationship of the induced therapeutic activity by virtue of the utilization of cNMDET and the degree of subsequent reparative changes is a dynamic transmuting process extending from various clinically imposed etiotropic mechanisms, such as locally clinically significant altered electron density patterns, one most prominent of which is referred to as bioelectromagnetic 'rifts' (the genesis and guiding vision of this patent method came from "standing on the shoulders of giants" as often expressed by others who feel so fortunate to follow, the clinical medicine discoveries related to electron density considerations as evolved and derived from such milestone discoveries as the Hall Effect in 1879 through the modified Drude Theory in 1900 to the Casimir Effect in 1947, Walker's synaptic tunneling model in 1970, the investigatory work of Bohm as expressed, in part, in Bohm's Model in 1980, and, most recently, extending from, the most contributory for today's endeavor, current dielectric and other bioenergetic tissue property theories lent us from the seminal contributions of quantization properties of bioelectromagnetic fields concepts), contributing collectively to altered macroscopic tissue properties and resultant dysfunction of clinical import on the macroscopic scale. Accordingly, the cNMDET method is designed, as part of its core reparative mechanisms, to reparatively target such processes as clinically significant altered electron density patterns, neuroplastic and metaplastic clinically contributory changes (including, but not limited to, inducing establishing metastable attractors).

The term 'desynchronization' as utilized herein is meant to refer to the reparative process afforded by the utilization of the cNMDET method. Desynchronization mechanistically addresses primary and secondary clinicopathologic states of derived 'synchronization', i.e., the process of enhancing undesirable pathologic processes such as, but not limited to, 'kindling' and 'dynamic entrainment'. The process of reparative desynchronization occurs throughout the CNS and PNS. An example would be the electrocortical clinicopathologic hypersynchronization and its related escalating autonomic hypervigilant state often associated with pain enhancing (exacerbating) processes which can often serve as the genesis of neuroexcitotoxicity, as well as, a host of other secondarily escalating neuropathologic states. Additionally, reparative decoupling (desynchronization) targets maladaptive neuroplastic and/or metaplastic synaptic connectivity and secondary pathologic up regulation. One of the many other clinically significant achievements involves the therapeutically inducing of reparative cortical metastable attractors.

Additionally, cNMDET enhances the supportive underlying critical neurometabolic capacities that are therapeutically induced resulting from the application of cNMDET and is of critical importance to the sustaining of the desired and therapeutically sought level of reparative processes. This concomitant enhancement of neurometabolic capacity prevents the negative consequences that are likely to result by accelerating production of metabolic decompensation from other therapeutic electrostimulatory applications.

These and other objectives of the present invention will become apparent to those skilled in this art upon a careful review of these specifications, drawings and claims.

BRIEF DESCRIPTION OF THE DRAWINGS

FIG. 1 is comprised of FIGS. 1A, 1B and 1C. FIG. 1C exemplifies one configuration of one component of the cNMDET placement in its preferred embodiment referred to as the 'Neural Tube Technique' (NTT). FIG. 1A illustrates the 'Cz' placement as derived by the intersection of the two measurements as described in electroencephalographic terminology of fifty percent (50%) of the distance from the nasion to inion distance and fifty percent (50%) of the preauricular point to preauricular point distance. This serves as the central point around which varying equidistances are calculated in the two basic planes corresponding on the dermis first to that of the longitudinal fissure of the brain and second to that of the central sulcus of the brain in the execution of the priming phase (electrostimulation) of the cNMDET method as is provided for by the patient-specific, controlling treatment protocol. FIGS. 1A, 1B and 1C, collectively, illustrate one electrode placement of the Neural Tube Technique which is comprised of the placement of one electrode of a particular electrostimulatory channel on the dermis correlated anatomically to the cephalic central midsagittal region referred to as 'Cz' (see above description) and the second of two electrodes of that particular channel on the dermis in the sacral central midsagittal plane, as illustrated in FIG. 1B, correlated anatomically to the cauda equina ('sacral outflow region'). FIG. 1C provides an overview illustration of the 'Neural Tube Technique'. In its preferred embodiment, the patient-specific, controlling treatment protocol specifies the progressive sequencing of electrode placements and other cNMDET parameters to include, but not be limited to, the formulation and extent of applicability of the priming, preconditioning and treatment phases.

FIG. 2 is comprised of FIGS. 2A, 2B and 2C, collectively illustrating one possible configuration/example of cNMDET placement integrating the Neural Tube Technique (NTT) with the targeting of a peripheral nerve placement, the median nerve illustrated in FIG. 2B as an example, and an overview of the potential central and peripheral neural pathway(s), more specifically illustrated in FIG. 2C. FIG. 2A refers to the placement of one of two coupled electrodes of a particular electrostimulatory channel on the dermis correlating to the cephalic midsagittal central plane position. Again referring to FIG. 2A, reference is made to the placement of the second of two coupled electrodes which collectively comprises one electrostimulatory channel on the dermis correlating to the sacral central midsagittal plane referred to in the NTT method application terminology as the 'sacral outflow area' otherwise known anatomically as correlating to the midsagittal sacral cauda equina region. This is referred to as the 'preconditioning phase' as may be provided for by the patient-specific, controlling treatment protocol which in this example preceded the therapeutic electrostimulatory phase and followed the priming phase, again, as would be provided for by the patient-specific, controlling treatment protocol. FIG. 2B illustrates one of many anticipated possible placements of the second of two electrodes of that particular channel on the dermis to deliver therapeutic stimulation transcutaneously to the underlying targeted nerve that comprises the intervening targeted neural pathway as provided for by the patient-specific, controlling treatment protocol, the median nerve in this instance. While in this particular paragraph of writing there is not a specific clinical case or diagnostic entity defined, it is likely that the patient-specific, controlling treatment protocol would stipulate in the treatment phase a patterned cNMDET approach in the event of an involved median nerve as in a Carpal Tunnel Syndrome diagnosis for example. In its preferred embodiment, the patient-specific, controlling treatment protocol specifies the sequencing of electrode placements and other cNMDET parameters to include extent of applicability and formulations of the priming, preconditioning and treatment phases as would be derived from that patient-specific, controlling treatment protocol which, as stated previously, is the subject of a post-election divisional patent application.

FIG. 3 is comprised of FIGS. 3A and 3B, collectively exemplifying one of many anticipated configuration of cNMDET placement integrating the 'Neural Tube' Technique with the targeting of a unilateral muscle targeted application, the trapezius muscle in this instance as may be provided for by the patient-specific, controlling treatment protocol. This specific example is one possible placement of many for a Myofascial Trigger Point treatment approach, again, as may be provided for by the patient-specific, controlling treatment protocol. In its preferred embodiment, the patient-specific, controlling treatment protocol specifies the sequencing of electrode placements and other cNMDET parameters to include the extent of applicability and formulations of the priming, preconditioning and treatment phases.

FIG. 4 is comprised of FIGS. 4A and 4B, collectively identified as a process flow chart illustrating a general process mapping of one configuration of the principle relationships between the 'central' facility and a stereotypic 'remote' facility wherein an application of the novel method of cNMDET, in its preferred embodiment, is relied upon to treat pain through the enabling utilization of a multifunctional apparatus/device in conjunction with the use of a clinical-outcomes knowledge-based algorithmic database/software program supported by a web-based, continuous, bidirectional, 'real-time' communications system (as 'real-time' as internet communication latencies allow). In utilizing the cNMDET method, in its preferred embodiment, the patient being treated would be continuously monitored by local licensed provider(s). Additionally, the data from the patient's continuous physiologic monitoring afforded by the appropriate multifunctional apparatus/device can be relied upon to assist the local provider's observations in monitoring the patient's progress and therefore impact at any time the controlling treatment protocol as deemed clinically necessary to protect the efficacy of the ongoing treatment and guard that patient's ultimate clinical outcome. In its preferred embodiment, the patient-specific, controlling treatment protocol specifies the sequencing of electrode placements and other cNMDET parameters to include extent of applicability and formulations of the priming, preconditioning and treatment phases.

DETAILED DESCRIPTION OF THE INVENTION

In its preferred embodiment, FIGS. 1, 2 and 3 refers to illustrative configurations of those anticipated for one or more therapeutic electrostimulatory channels comprised of two electrodes per electrostimulatory channel electronically coupled for the purpose of delivering therapeutic electrostimulation either unidirectional or bidirectional comprised of patterns that include varying alternating polarities, varying intensities, pulse-widths and waveform patterns (formulated mixture of square waves, trains of square waves and/or spikes) to deliver/utilize this novel method known as the Coupled Neuraxial Mesoscopic Desynchronization Electrostimulation Therapy (cNMDET) in accordance with the controlling treatment protocol designed to reparatively modulate the central nervous system (CNS) [regions of the brain, spinal cord and intervening structures including, but not limited to, the underlying (contributory) clinicopathologic mechanisms of the autonomic nervous system (ANS)] and clinically involved components of the peripheral nervous system (PNS) variably coupled as provided for by the controlling treatment protocol in such a manner as to apply this therapeutic electrostimulation along the coursing path (longitudinally) of the targeted neural pathway over a segment and/or in its entirety (the full expanse possible of the CNS and PNS), as well as, the utilization of patterned applications for involved joints, muscles, fascia, ligaments, tendons and areas involved in inflammatory processes of clinical significance accomplished through the application of, preferably, but not limited to, Coupled Neuraxial Transcutaneous Electrical Nerve Stimulation (cNTENS) and Coupled Neuraxial Transcranial Direct Stimulation (ctDCS$_n$) for the purpose of treating pain.

In the terminology associated with the novel method known as Coupled Neuraxial Mesoscopic Desynchronization Electrostimulation Therapy (cNMDET), the term 'coupled neuraxial' is used to denote the method of providing therapeutic electrostimulation 'longitudinally' utilizing one or more electrostimulatory channels (two electronically coupled electrodes per channel or configured in a scalable array) to the targeted neural pathway areas. Accordingly, this would apply to all intervening tissue, nervous tissue, muscle, fascia, tendons, ligaments, joints and immunologic inflammatory processes as may be found within the patterned applications.

In the terminology associated with the novel method known as Coupled Neuraxial Mesoscopic Desynchronization Electrostimulation Therapy (cNMDET), the term 'patterned application' is used to denote the use of one or more electrostimulatory channels (two electronically coupled electrodes per channel or configured in a scalable array) that is positioned according to the controlling treatment protocol for application of cNMDET (with full consideration of targeted neural pathways as addressed earlier) coupled to a targeted area such as a muscle(s), connective tissue(s), myofascial trigger point(s), joint(s) and/or area(s) of inflammation. Accordingly, this would apply to all intervening tissue, nervous tissue, muscle, fascia, tendons, ligaments, joints and immunologic inflammatory processes as may be found within the patterned applications.

In the terminology associated with the novel method known as Coupled Neuraxial Mesoscopic Desynchronization Electrostimulation Therapy (cNMDET), the term 'desynchronization' refers to the reparative mechanism of the 'uncoupling' of aberrantly imposed synaptic connectivity, maladaptive loops and the reversing of hyperexcitability of synaptic activity trajectories. Its action targets primary and secondary 'hypersynchronization', i.e., the process of contributing to undesirable pathologic processes such as 'kindling' and 'dynamic entrainment' (including metaplastic clinicodynamics). The process of reparative desynchronization can occur throughout the CNS and PNS. One example would be the electrocortical clinicopathologic hypersynchronization associated with various hyperexcitability states and its resultant tendency to clinically up-regulate autonomic hypervigilant dysfunctional states often associated with pain exacerbating processes that can often serve as the genesis of neuroexcitotoxicity as well as a host of other neuropathologic states.

In the terminology associated with the novel method known as Coupled Neuraxial Mesoscopic Desynchronization Electrostimulation Therapy (cNMDET), the terms 'couple, coupled and/or coupling' describes the configuration of one electrostimulatory channel wherein the channel is comprised of two electrodes electronically configured in an individually programmable manner. Coupled electrodes are configured for scalable arrays as specified by the applicable controlling treatment protocol. Coupled electrodes are used to deliver either unidirectional or bidirectional patterns of therapeutic electrostimulation in the delivery of the novel method known as cNMDET comprised of electrostimulatory patterns [percent composition of spikes, trains of squarewave pulses (including squarewave 'roll-off' specifications) and/or combinations or mixtures of same with additional specification for electrostimulation intensity, pulse-width, and polarity, of each electrostimulatory pulse with additional specification of each delivery window (duration) for each treatment site] in accordance with the controlling treatment protocol designed to therapeutically modulate the CNS (including, but not limited to, the ANS), PNS, musculature, fascia, tendons, ligaments, joints and immunologic inflammatory processes for the purpose of treating pain.

In the terminology associated with the novel method known as Coupled Neuraxial Mesoscopic Desynchronization Electrostimulation Therapy (cNMDET), the term 'mesoscopic' describes one of the scales of targeted therapeutic activity upon which the cNMDET method functions. The cNMDET method is not limited to, the targeting of activity in the 'mesoscopic' scale but certainly derives initial therapeutic contributions from same. The mesoscopic scale refers to the subdiscipline of condensed-matter that focuses on the properties of solids in a size range intermediate between bulk matter and individual atoms or molecules. Stated differently, the mesoscopic scale as used herein refers to the scale at which one can reasonably discuss the properties of a material or phenomenon without having to discuss the behavior of individual atoms. The causal relationship of the induced therapeutic activity by virtue of the utilization of cNMDET and the degree of subsequent reparative changes is a dynamic transmuting process extending from various therapeutically induced etiotropic mechanisms such as alteration of electron density patterns and others contributing collectively to macroscopic tissue properties, therefore resulting in observable anatomy and physiology. As part of this process neuroplastic and metaplastic transmuting changes (including, but not limited to, inducing brain-based metastable attractors) are reparatively recruited.

In the terminology associated with the novel method known as Coupled Neuraxial Mesoscopic Desynchronization Electrostimulation Therapy (cNMDET), the phrase 'Neural Tube Technique' (NTT) is used to generally describe one configuration providing for the delivery of therapeutic electrostimulation as a component of cNMDET as may be specified by the controlling protocol. NTT is the coupling of electrostimulatory electrodes that transcutaneously provide therapeutic electrostimulation to the brain extending through the intervening neural structures and spinal cord, to include, but not be limited to, the cauda equina region ('sacral outflow area'). The anatomical expanse, i.e., distance between electrostimulatory electrodes may be quite narrow ranging to the full incorporation of the brain's most superior/rostral extreme, coupled to the spinal cord's most inferior/caudal extreme and extending to the cauda equina region ('sacral outflow area') as stipulated by the controlling treatment protocol. This expanse would incorporate all the potential coupled placements (including arrays of electrodes) as space would allow, reasonably contingent on the choice of electrodes and defined areas of clinical significance contained therein. It is anticipated that one or more coupled electrostimulatory electrodes (including arrays of electrodes) are to be used as provided for by the controlling treatment protocol.

In the terminology associated with the novel method known as Coupled Neuraxial Mesoscopic Desynchronization Electrostimulation Therapy (cNMDET), the term 'priming' is used generally to describe, in its preferred embodiment, a technique and/or approach that is used to promote increased neural pathway synaptic associative activity and volume related cooperativity in a preparatory manner to the delivery of the pre-conditioning phase which precedes the treatment phase of electrostimulation to the targeted neural pathway. Generally, the primary target is the CNS with secondary recruitment of the PNS. Priming is accomplished with formulated electrostimulations that may be efferent (in the case of vertically desired vectors) and/or afferent (in the case of horizontally desired vectors) or some combination of the two, anodal and/or cathodal, including, varying electrostimulatory patterns [percent composition of spikes, trains of squarewave pulses (including squarewave 'roll-off' specifications) and/or combinations or mixtures of same with additional specification for electrostimulation intensity, pulse-width, and polarity, symmetric and asymmetric configurations of each electrostimulatory pulse with additional specification of each delivery window (duration) for each treatment site]. In the initial priming phase, two cephalic planes are targeted. First, there is the midsagittal central plane, parallel to the longitudinal fissure. Second, there is the mid-coronal plane, perpendicular to the longitudinal fissure roughly corresponding to the central sulcus allowing for normal anatomical variance. Electrostimulatory channels each with two coupled placements has its two electrodes placed at varying distances as provided for by the controlling treatment protocol equidistance from Cz first parallel then perpendicular to the longitudinal fissure along the central sulcus plane. In considering alternative placements associated with a centered Cz placement in the two aforementioned planes (equidistance from Cz first parallel then perpendicular to the longitudinal fissure along the central sulcus plane) and in the additional consideration of a particular electrode use, selecting a disc electrode (one of the many provided for) would, as a practical matter address limiting variability of inter-visit and inter-provider electrode placement, by considering an incremental progression of distance for any one disc electrode targeted placement may be 0.5 cm (5 mm) based on the standard disc electrode diameter of 10 mm tempered by considerations of normal anatomical variances as may be demonstrated to exist during the course of treatment. The controlling treatment protocol precisely provides for the starting and progression of positioning of electrode placement increments and may be impacted (revised for the sake of increasing the efficacy of each treatment) as treatments progress.

In the terminology associated with the novel method known as Coupled Neuraxial Mesoscopic Desynchronization Electrostimulation Therapy (cNMDET), the term 'preconditioning' in its preferred embodiment is utilized after the 'priming' phase and is used to generally describe a technique or approach that is used in a preparatory manner to the delivery of reparative electrostimulation (cNMDET) therapy to the targeted neural pathway (either to a segment and/or the entire neural pathway). Preconditioning may be accomplished with efferent and/or afferent or some combination of the two, anodal and/or cathodal, including, symmetric and asymmetric biphasic waveforms as specified by the controlling treatment protocol. Additionally, the pattern of electrostimulation waveforms is of critical importance. The controlling treatment protocol should specify the electrostimulatory patterns [percent and order of combinations of spikes, trains of squarewave pulses (including 'roll-off' specifications) and/or combinations or mixtures of same with additional specification for varying intensity, pulse-width and polarity of each stimulation as well as delivery window (duration) for each treatment site electrode placement montage].

In its preferred embodiment, treatment protocols would be developed with the assistance of a clinical-outcomes knowledge-based algorithmic database/software program, one such program known as the AlgoNeuroMatrix (ANM) which is the subject of a post-election divisional patent application to be subsequently filed. In its preferred embodiment, each treatment protocol is patient-specific and is developed on a visit by visit basis modifiable on the fly by the contemporaneous patient data produced during each treatment. It bears emphasis that each patient-specific, controlling treatment protocol should be adaptable within each visit according to each patient's contemporaneous response during same and supported by a continuous web-based bidirectional communications protocol. Lastly, in addition to the contributions of a clinical-outcomes knowledge-based algorithmic database/software program, a network of professional providers, and various clinical resources, collectively referred to as the Clinical Triage Resource contributes to the development of treatment protocols for the purpose of improving clinical outcomes for patients being treated for pain.

In its preferred embodiment for the utilization of the cNMDET method the clinical-outcomes knowledge-based algorithmic database/software program responds to a prescribed, prompted, comprehensive set of clinical data uploaded from a remote facility to a central facility by way of a continuous web-based connection. Once the uploaded data by the central facility for that individual patient for that individual visit has been evaluated and a patient-specific, controlling treatment protocol formulated and downloaded via the web-based connection providing for the formulated treatment protocol is then downloaded from the central facility to the remote originating facility and additionally affords the capacity for continuous monitoring of the patient and periodic treatment protocol amendments as may be clinically indicated by the changes reflected in the ongoing physiologic monitoring data during each visit, patient reporting and contemporaneous observations of the remote facility's licensed provider. One example of a clinical-outcomes knowledge-based algorithmic database/software program is the subject of a post-election divisional patent to be subsequently filed. It is anticipated that a few strategically placed central facilities can support a full national and international distribution of 'remote' facilities.

cNMDET is considered to be a 'therapeutic multiplier' when used concomitantly with other treatment approaches and because of cNMDET's broad compatibility with all other established treatment approaches, cNMDET is considered to be 'intermodality'.

FIG. 1 is comprised of FIGS. 1A, 1B and 1C. FIG. 1C exemplifies one configuration of one component of the cNMDET placement in its preferred embodiment referred to as the 'Neural Tube Technique' (NTT). FIG. 1A illustrates the 'Cz' placement as derived by the intersection of the two measurements as described in electroencephalographic terminology of fifty percent (50%) of the distance from the nasion to inion distance and fifty percent (50%) of the preauricular point to preauricular point distance. This serves as the central point around which varying equidistances are calculated in the two basic planes corresponding on the dermis first to that of the longitudinal fissure of the brain and second to that of the central sulcus of the brain in the execution of the priming phase (electrostimulation) of the cNMDET method as is provided for by the controlling treatment protocol. FIGS. 1A, 1B and 1C, collectively, illustrate one electrode placement of the Neural Tube Technique which is comprised of the placement of one electrode of a particular electrostimulatory channel on the dermis correlated anatomically to the cephalic central midsagittal region referred to as 'Cz' (see above description) and the second of two electrodes of that particular channel on the dermis in the sacral central midsagittal plane, as illustrated in FIG. 1B, correlated anatomically to the cauda equina ('sacral outflow region'). In its preferred embodiment, the controlling treatment protocol specifies the progressive sequencing of electrode placements and other cNMDET parameters to include, but not be limited to, the formulation and extent of applicability of the priming, preconditioning and treatment phases.

FIG. 2 is comprised of FIGS. 2A, 2B and 2C collectively illustrating one possible configuration/example of cNMDET placement integrating the Neural Tube Technique (NTT) with the targeting of a peripheral nerve placement. FIG. 2A refers to the placement of one of two coupled electrodes of a particular electrostimulatory channel on the dermis correlating to the cephalic midsagittal central plane position. Again referring to FIG. 2A, reference is made to the placement of the second of two coupled electrodes which collectively comprises one electrostimulatory channel on the dermis correlating to the sacral central midsagittal plane referred to in the NTT method application terminology as the 'sacral outflow area' otherwise known anatomically as correlating to the midsagittal sacral cauda equina region. This is referred to as the 'preconditioning phase' which in this example preceded the therapeutic electrostimulatory phase and followed the priming phase. FIG. 2B illustrates one of many anticipated possible placements of the second of two electrodes of that particular channel on the dermis to deliver therapeutic stimulation transcutaneously to the underlying targeted nerve that comprises the intervening targeted neural pathway, FIG. 2C provides for an overview pathway illustration, as provided for by the controlling treatment protocol, the median nerve in this instance. While in this particular paragraph of writing there is not a specific clinical case defined, it is likely that the controlling treatment protocol would stipulate in the treatment phase a patterned cNMDET approach in the event of an involved median nerve as in a Carpal Tunnel Syndrome diagnosis. In its preferred embodiment, the controlling treatment protocol specifies the sequencing of electrode placements and other cNMDET parameters to include extent of applicability and formulations of the priming, preconditioning and treatment phases as would be derived from the clinical-outcomes knowledge-based algorithmic database/software program which, as stated before, is the subject of a post-election divisional patent application.

FIG. 3 is comprised of FIGS. 3A and 3B collectively exemplifying one anticipated configuration of cNMDET placement integrating the 'Neural Tube Technique' with the targeting of a unilateral muscle targeted application, the trapezius muscle in this instance. This specific example is one possible placement for a Myofascial Trigger Point treatment approach. In its preferred embodiment, the controlling treatment protocol specifies the sequencing of electrode placements and other cNMDET parameters to include extent of applicability and formulations of the priming, preconditioning and treatment phases.

FIG. 4 is comprised of FIGS. 4A and 4B collectively identified as a process flow chart illustrating a general process mapping of one configuration of the principle relationships between the 'central' facility and a stereotypic 'remote' facility wherein in its preferred embodiment an application of the novel method of cNMDET is relied upon to treat pain through the enabling utilization of a multifunctional apparatus/device in conjunction with the use of a clinical-outcomes knowledge-based algorithmic database/software program supported by a web-based, continuous, bidirectional, 'real-time' communications system (as 'real-time' as internet communication latencies allow). In utilizing the cNMDET method, in its preferred embodiment, the patient being treated would be continuously monitored by local licensed providers. Additionally, the data from the patient's continuous physiologic monitoring afforded by the multifunctional apparatus/device can be relied upon to assist the local provider's observations in monitoring the patient's progress and therefore impact at any time the controlling treatment protocol as deemed clinically necessary to protect the efficacy of the ongoing treatment and guard that patient's ultimate clinical outcome. In its preferred embodiment, the controlling treatment protocol specifies the sequencing of electrode placements and other cNMDET parameters to include extent of applicability and formulations of the priming, preconditioning and treatment phases.

In the preferred embodiment of this method patent it is anticipated that the term 'electrode' where referenced applies to a range of delivery contacts/methods, including some combination of wired or wireless electrodes, handheld probe electrodes, electrode gloves, needles and/or skin affixed electrodes such as, but not limited to, silver-silver chloride, tin or gold disk or adhesive pad electrodes and/or active dry, configured in a single, coupled or array patterned electrodes.

In the preferred embodiment of this method patent the electrostimulatory apparatus/device utilized to deliver this novel patent method, cNMDET, should be used in full compliance of the FDA approved manufacturer's instructions and/or recommendations which includes, but is not limited to, adequate skin prep to assure appropriate levels of dermal resistance and the use of specified/recommended electrocoupling substances/techniques applied to the electrodes or other delivery mechanisms.

The cNMDET method is designed to therapeutically modulate the CNS (including, but not limited to, targeted clinicodynamics attributable to the ANS), PNS, musculature, fascia, tendons, ligaments, joints and immunologic inflammatory processes for the purpose of treating pain as specified by the patient-specific, controlling treatment protocol.

In its preferred embodiment, each controlling treatment protocol application and patient response as measured by the multifunctional Algotron's battery of diagnostic and physiologic real-time monitors, as well as, continuously elicited reports from the patient by the attendant local licensed provider, who is making their own contemporaneous clinical observations as the treatment progresses, is monitored for the targeted clinical effect throughout each treatment visit. Each treatment protocol is designed to be continuously, i.e., 'real-time', monitored and are modifiable within each treatment visit. The multifunctional Algotron apparatus/device is the subject of a post-election divisional patent to be subsequently filed.

Emanating from a collection of clinical outcomes data is in its preferred embodiment with one configuration/application utilizing an artificial intelligence (AI) database engine, one such program herein referred to as the AlgoNeuroMatrix (ANM) which is a clinical-outcomes knowledge-based algorithmic database/software program which is the subject of a divisional patent application to follow. This program is designed to be used to calculate patient-specific, controlling treatment 'protocols' to be utilized by a multifunctional treatment apparatus/device, one such apparatus/device known as the Algotron is also the subject of a divisional patent application. The artificial intelligence (AI) database engine is a continuously updated integration of patient clinical data regarding presenting symptomatology with a wide variance of individualized treatment protocols over the evolution of many individual patient cases and their related outcomes over time. In one configuration, the artificial intelligence (AI) database engine responds to a prescribed prompted comprehensive set of clinical data uploaded from a remote facility [remote originating, on-site treating provider on a patient-specific, treatment visit by treatment visit basis (beyond the initial, extensive and data-intensive intake visit)] to a central facility by way of a continuous web-based connection. This web-based connection provides for the formulated treatment protocol to be downloaded from the central facility to the remote originating facility and provides for the continuous monitoring of the patient and periodic treatment protocol amendments as may be indicated by the changes reflected in the continuous physiologic monitoring data, patient reporting and/or remote local licensed facility Provider. The artificial intelligence (AI) database engine is the subject of a post-election divisional patent to be subsequently filed.

The artificial intelligence (AI) database engine produces preliminary treatment protocols for review and final approval by the central facility 'Clinical Triage Resource', a network of professional providers, and various clinical resources, collectively referred to as the Clinical Triage Resource, for each individualized, i.e., patient and visit specific, protocol defining the sequencing of electrode stimulation treatment windows, placement configuration, timing, and stimulation parameters collectively referred to as the patient-specific, controlling treatment protocol on a visit by visit basis. Critically, the Clinical Triage Resource and the artificial intelligence (AI) database engine work simultaneously and continuously to monitor each treatment visit as it progresses as afforded by the remote facility multifunctional apparatus/device communicating over a continuous, web-based, bidirectional communications connection.

Although the present invention (method) has been described with reference to preferred embodiments, changes may be made in form without departing from the scope of the invention (method). Having described and illustrated the principles of the present invention (method), it should be apparent that the invention (method) can be modified in arrangement and detail without departing from such principles. The present invention (method) should not be limited, for instance, to various other electrostimulatory and/or diagnostic and/or physiologic monitoring modalities and/or to other devices but rather can be applied to any medical device having parameters than can be remotely programmed responsive to locally or remotely input patient criteria. Accordingly, the scope of the present invention (method) shall be governed by the following claims.

Additionally, cNMDET enhances the supportive underlying neurometabolic capacities that are therapeutically induced resulting from the application of cNMIDET and is of critical importance to the sustaining of the desired and therapeutically sought level of reparative processes which has been, heretofore, woefully lacking in all other therapeutic approaches.

What is claimed is:

1. A method of Coupled Neuraxial Mesoscopic Desynchronization Electrostimulation Therapy (cNMDET) for applying ambulatory, non-invasive therapeutic electrostimulatory modalities, comprising mechanisms of action that are reparative, palliative and support adaptive recovery, in a preferred embodiment utilizing Coupled Neuraxial Transcutaneous Electrical Nerve Stimulation (cNTENS) and Coupled Neuraxial Transcranial Direct Stimulation (ctDCS$_n$), wherein the electrostimulatory modalities are configured to treat both acute and chronic pain, the method comprising;
   placing a combination of at least two progressively sequenced electrodes on clinically targeted nerve areas, wherein the clinically targeted nerve areas establish a targeted neural pathway, the targeted neural pathway including at least one of;
      a) central nervous system (CNS) sites,
      b) underlying contributory clinicopathologic mechanisms of autonomic nervous system (ANS) sites and
      c) clinically involved components of peripheral nervous system (PNS) sites;
      wherein the CNS sites are comprised of brain regions, spinal cord regions and intervening structures;
   applying therapeutic electrostimulation along a longitudinally coursing path of the targeted neural pathway,
      wherein the longitudinally coursing path consists of targeted neural system pathways, and
   wherein an additional combination of progressively sequenced electrostimulation electrodes further includes a patterned placement of the additional electrostimulation electrodes in an array of electrodes configured to treat involved joints, muscles, fascia, ligaments, tendons and areas involved in an inflammatory process.

2. The method for applying the therapeutic electrostimulatory modalities according to claim 1 wherein:
   in a preferred embodiment, the at least two progressively sequenced electrodes are further comprised of one or more stimulation channels including configurations of individually programmable electrode arrays with two electronically coupled electrode outputs per channel.

3. The method for applying the therapeutic electrostimulatory modalities according to claim 1 wherein:
   in a preferred embodiment, a 'Neural Tube Technique' (NTT) utilized in the priming, conditioning and treatment phases as may be specified by the controlling patient-specific treatment protocol is used
   which is comprised of a configuration of the at least two coupled electrostimulatory electrodes to provide therapeutic electrostimulation transcutaneously
   with one of the two coupled electrodes is placed at the central vertex (CZ) and the second placed according to the controlling patient-specific treatment protocol either to cutaneously approximate either the conus medullaris or alternatively the cauda equina region rsacral outflow area)
   wherein an additional combination of progressively sequenced electrostimulation electrodes may be utilized as may be specified by the controlling patient-specific treatment protocol
   to the CNS incorporating the region from the central vertex (CZ) to the cauda equina region ('sacral outflow area').

4. The method for applying the therapeutic electrostimulatory modalities according to claim 1 wherein:

in a preferred embodiment, the therapeutic electrostimulation is provided longitudinally, by a coupled neuraxial field consisting of the CNS sites and the clinically involved components of the PNS in a varying coupled progressively sequenced manner according to a patient-specific controlling treatment protocol wherein the therapeutic electrostimulation modulation is applied along the longitudinal coursing path of at least one of the targeted neural pathway or a targeted segment or the entire length of the segment.

5. The method for applying the therapeutic electrostimulatory modalities according to claim 1 wherein:

in a preferred embodiment, formulated therapeutic electrostimulation modulation is provided and is comprised of the pattered application of the electrostimulatory electrodes applied to the involved, muscles, fascia, ligaments, tendons, joints and areas of inflammatory processes as prescribed by a patient-specific controlling treatment protocol wherein at least one of one or more channels consisting of two electrodes per channel are electronically coupled or the array of electrodes is electronically coupled for programming across the array for the targeted treatment area or intervening neural pathway.

6. The method for applying the therapeutic electrostimulatory modalities according to claim 1 wherein:

in a preferred embodiment, a patient-specific controlling treatment protocol contains a 'priming phase', wherein the 'priming phase' qualitatively prepares the targeted neural pathway(s) for an initiation of a promotion of an increased recruitment of processes of synaptic associative activity, and cooperativity primarily in the CNS sites with secondary influences in the PNS sites in preparation for a preconditioning treatment phase.

7. The method for applying the therapeutic electrostimulatory modalities according to claim 1 wherein:

in a preferred embodiment, a patient-specific controlling treatment protocol contains a 'preconditioning phase' that establishes/promotes timed, therapeutic volume modulation which includes consideration of increased activity of a property of a process of associative activity and cooperativity and therapeutic electrostimulation of a targeted CNS site and to prescribed portions of the CNS, to achieve a threshold of an increased level of receptivity to the subsequent treatment phase.

8. The method for applying the therapeutic electrostimulatory modalities according to claim 1 wherein:

in a preferred embodiment, enhanced supportive neurometabolic capabilities are therapeutically induced resulting from the application of cNMDET.

* * * * *